United States Patent [19]

Takahashi et al.

[11] Patent Number: 5,334,518
[45] Date of Patent: Aug. 2, 1994

[54] PROCESS FOR PREPARATION OF GAMMA-PYRONE DERIVATIVES

[75] Inventors: Hidehiko Takahashi, Tokyo; Katsumi Imada, Funabashi; Akira Motoshio, Kodaira, all of Japan

[73] Assignee: Yakurigaku Chuo Kenkyusho, Tokyo, Japan

[21] Appl. No.: 970,859

[22] Filed: Nov. 3, 1992

[51] Int. Cl.⁵ ............................................. C12P 17/06
[52] U.S. Cl. .................................... 435/125; 435/822; 549/418
[58] Field of Search ................ 435/125, 822; 549/418

[56] References Cited

U.S. PATENT DOCUMENTS 3,130,204 4/1964 Tate et al. ............................ 549/418
3,654,316 4/1972 Oga et al. ............................ 549/418
4,221,723 9/1980 Oga et al. ............................ 549/418

FOREIGN PATENT DOCUMENTS 1814341 7/1969 Fed. Rep. of Germany ...... 549/418
1033511 6/1966 United Kingdom ................ 549/418

OTHER PUBLICATIONS

Chemical Abstracts, vol. 97, No. 4, 26 Jul. 1982, Columbus, Ohio, US; abstract No. 28588z.
Database WPI Section Ch, Week 9314, Derwent Publications Ltd., London, GB; Class D13, AN 93-111890.
Chemical Abstracts, vol. 72, No. 11, 16 Mar. 1970, Columbus, Ohio, US; abstract No. 52026u.
Chemical Abstracts, vol. 57, No. 6, 17 Sep. 1962, Columbus, Ohio, US; abstract No. 7718e.
Chemical Abstracts, vol. 50, No. 22, 25 Nov. 1956, Columbus, Ohio, US; abstract No. 16964d.

*Primary Examiner*—Herbert J. Lilling
*Attorney, Agent, or Firm*—Armstrong, Westerman, Hattori, McLeland & Naughton

[57] ABSTRACT

Disclosed is a novel process for the production of pyrocomenic acid [3-hydroxy-4(1H)-pyran-4-one and rubiginol [3,5-dihydroxy-4(1H)-pyran-4-one, which are starting materials for synthesis of maltols useful as food spices as well as additives for cosmetics.

The chemical reactions possibly taking place in the fermentation and the heating post-treatment thereof in the present invention are shown as follows:

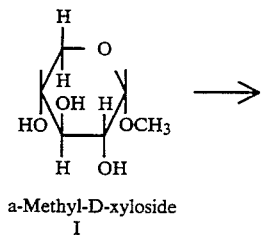

a-Methyl-D-xyloside
I

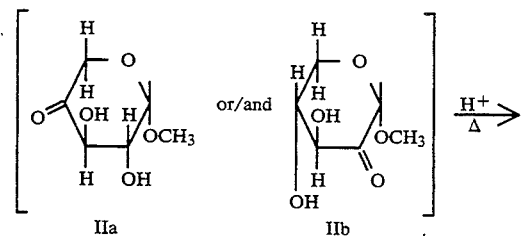

IIa    IIb

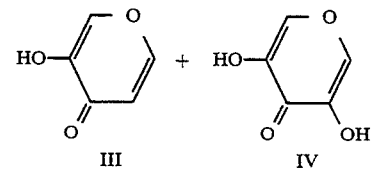

III    IV

The microorganisms usable in the above oxidation fermentation include *Gluconobacter rubiginosus* IFO 3244, *Gluconobacter suboxydans* IFO 3254, *Gluconobacter melanogenus* IFO 3293, *Pseudomonas fluorescens* IFO 3081, *Erwinia carotovara* IFO 3380 etc.

4 Claims, No Drawings

PROCESS FOR PREPARATION OF GAMMA-PYRONE DERIVATIVES

BACKGROUND OF THE INVENTION

1. Field of the Invention

The present invention relates to a novel process for the preparation of γ-pyrone derivatives including pyrocomenic acid, [3-hydroxy4(1H)-pyran-4-one and rubiginol, [3,5-dihydroxy-4(1H)-pyran-4-one, which are starting materials for synthesis of maltols useful as food spices as well as additives for cosmetics.

2. Prior Art

Maltols are known to be conventionally produced for example by the following methods:

U.S. Pat. No. 3,130,204 (1947) and Spielman M.A. et al, "J. Am. Chem. Soc.", 1947, 69 2908 disclose the method wherein after hydroxyl groups of kojic acid obtained by fermentation are protected, its primary alcohol group is oxidized, next the protecting group is removed, then the resulting material is subjected to decarboxylation reaction to form pyrocomenic acid, further hydroxymethylated and thereafter reduced to obtain maltols.

Japanese Patent Publication Sho 45-16204 discloses the method wherein 2,5-diketogluconic acid is heated under an acidic condition, the resulted comenic acid is decarboxylated to form pyrocomenic acid, which is followed by the same manners as above to obtain maltols. Shono et al, "Tetrahedron Lett., 1976, 1963 discloses the method wherein furfurals are led to 2,5-dimethoxyfuran derivatives through electlytic reaction, said derivatives are placed under an acidic condition to take place ring-formation reactions, thereby obtaining β-pyrone derivatives, further the resultants are subjected to alkylation, expoxydation and acidic condition to obtain maltols.

As seen above, maltols are produced through a considerably large number of the preparation steps. In addition, their yields are not necessarily satisfactory. Further there are also cases wherein relatively expensive chemicals are used.

In the light of such a present status, the present inventors have extended our studies to develop various methods for economically and simply preparing pyrocomenic acid which is to be the key compound for the preparation of maltols.

SUMMARY OF THE INVENTION

The object of the present invention is to provide a process for the production of 3-hydroxy-4(1H)-pyran-4-one and 3,5-dihydroxy-4(1H)-pyran-4-one, which comprises oxidation-fermentation of 1-alkyl-substituted-aldopentoses, followed by heating the resulting fermentation product under an acidic condition.

DESCRIPTION OF THE INVENTION

The present inventors have turned their attention to aldopentoses because pyrocomenic acid has five carbon atoms, and found that D-xylose, which is one of said aldopentoses, is first methoxylated at its 1-positioned carbon atom to form α-methylxyloside to be used as a carbon source, and then said xyloside is subjected to oxidation-fermentation by using microorganism of Gluconobacter rubiginosus IFO 3244, and thereafter, the solution resulting from completion of the fermentation is adjusted to pH 1.0 and then heated to form the objective pyrocomenic acid.

Based on the above finding, the present invention has been accomplished, and at that time, the byproduction of rubiginol has been also found. Aida et al, "Japan Soc. of Agricultural Chemistry" 28 517 (1969) reports that various kinds of metabolites including xylonic acid and in addition, rubixylic acid were obtained from D-xylose itself by the fermentation of microorganism similar to the above. However no example of formentation using α-methylxyloside as a carbon source has been known yet. Further, such formation of pyrocomenic acid as in the present invention has been not known at all.

Furthermore, the present inventors have found that after α-methylation of the aldopentoses other than D-xylose, which are L-xylose, D- and L-arabinoses, lyxose and ribose, fermentation and its after-treatments thereof were likewise conducted to form also pyrocomenic acid and ribiginol.

In addition, besides the above microorganisms our studies were extended to oxidation fermentation microorganisms such as Gluconobacter suboxydans, G. melanogenus, Pseudomonas fluoresces, Erwina carotovora, etc., thereby having accomplished the present invention based on the discovery of the almost similar results being also obtainable.

Chemical reaction formula concerning the above matters are given as follows:

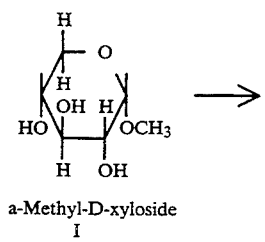

a-Methyl-D-xyloside
I

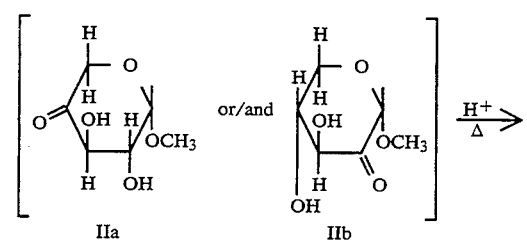

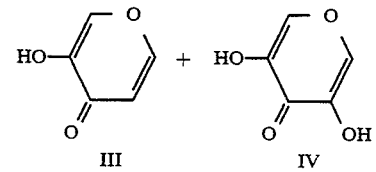

Also, these experimental results are shown in the following Table 1:

TABLE 1

Formations of pyrocomenic acid and rubiginol from alopentoses

| Pentose | D or L | Protecting group at $C_1$ | Strain used | pH | Pyrocomenic acid (fermentation 6th day) Productivity | Rubiginol (formentation 6th day) Productivity |
|---|---|---|---|---|---|---|
| Xylose | D | H | A | 3.7 | — | — |
| | D | Me | A | 4.9 | +++ | + |

TABLE 1-continued

Formations of pyrocomenic acid and rubiginol from alopentoses

| Pentose | D or L | Protecting group at $C_1$ | Strain used | pH | Pyrocomenic acid (fermentation 6th day) Productivity | Rubiginol (formentation 6th day) Productivity |
|---|---|---|---|---|---|---|
| | D | Me | B | 5.1 | + | ± |
| | D | Me | C | 4.9 | +++ | + |
| | D | Me | D | 8.4 | + | ± |
| | D | Me | E | 8.3 | — | — |
| | D | Et | A | 4.9 | + | ± |
| | L | H | A | 4.9 | — | — |
| | L | Me | A | 5.0 | ± | — |
| Arabinose | D | H | A | 4.5 | — | — |
| | D | Me | A | 5.0 | ++ | ± |
| | L | H | A | 4.2 | — | — |
| | L | Me | A | %.) | + | ± |
| Lyxose | D | H | A | 4.8 | — | — |
| | D | Me | A | 5.0 | +++ | ± |
| | L | H | A | 5.0 | — | — |
| | L | Me | A | 4.7 | ± | ± |
| Ribose | D | H | A | 4.7 | — | — |
| | D | Me | A | 4.9 | ++ | ± |
| | L | Me | A | 4.9 | + | ± |

Note:
Strains used of microorganisms:
A: *Gluconobactor rubiginosus* IFO 3244
B: *Gluconobacter melanogenus* IFO 3293
C: *Gluconobacter suboxydans* IFO 3254
D: *Erwinia carotovora* IFO 3380
E: *Pseudomonas fluorescens* IFO 3081
Productivity of γ-pyrone:
±: <50 mg
+: 50-100 mg
++: 100-300 mg
+++: >300 mg The experimental results in Table 1 were obtained in the following manner:

20 ml of the fermentation filtrate picked up was adjusted with surfuric acid to pH 1.0 and then treated under heating at 120° C. for 30 minutes. The resultant was concentrated in vacuo to 2.0 ml and then subjected to a fractional thin layer chromatography (eluent solvent mixture ... chloroform: ethanol=10:1) to scratch off each fraction corresponding to chromophoric position each of pyrocomenic acid and nibiginol. The resulting fractions were extracted with chloroform, concentrated in vacuo upto a dry solid to which water was added to provide for a quantative analysis. According to the quantative analysis of Ishige et al method (Journal of Japan Agricultural Chemistry, Vol. 40, No. 10, pp 353-358, 1966), 1.0 ml of 10% surfuric acid, 0.5 ml of 5% $Fe_2(SO_4)_3 \cdot XH_2O$, 0.1 ml of sample and 3.4 ml of distilled water were added in the order. From the resulting redish violet color, the respective amounts of pyrocomenic acid and rubiginol were sought by means of determination of 500 nm extinction intensity. For the standard lines in quantative analysis of pyrocomenic acid and rubiginol, the samples obtained by the method of Example 1 were used.

Composition of Culture Medium
ldopentoses: 2.0-3.0% (alkylated a ldopentoses: 2.73-3.61%), yeast extract: 1.5%, polypepton: 1.5%, glycerol: 1.5%, ($CaCO_3$: 0.75% (separately sterilized).
D-xylose: 3.0%, L-xylose: 2.3%, D-arabinose: 3.0%, L-arabinose: 3.0%, D-lyxose: 2.3%, D-ribose: 3.0%, Me-D-xylose: 3.64%, Et-D-xylose: 3.28%, Me-L-xylose: 2.73%, Me-D-arobinose: 3.28%, Me-L-arabinose: 3.28%, Me-D-lyxose: 2.73%, Me-D-lyxose: 2.73%, Me-D-ribose: 3.28%.

As shown in Table 1, formation of γ-pyrones from all the α-methylated-D-aldopentoses has been observed. Also, α-ethylated case has given almost similar results. On the contrary, no formation of γ-pyrones has been observed from α-non-methylated aldopentoses.

When α-methylated aldopentoses were subjected to oxidation-fermentation, it can be supposed that firstly intermediates IIa and/or IIb, which are shown in the parenthesis in the afore-mentioned reaction scheme, are formed, and then β-OH leaving or the like from said intermediates will bring about formation of the objective γ-pyrones, in view of many examples of studies in which hexoses have been fermented using the above-mentioned microorganism. The existence of said intermediates IIa and/or IIb could be presumed because reduction of Fehling solution is observed with proceeding of the fermentation, as shown in Table 2 of Example 1, despite the starting material, α-methyl-D-xylose should have no power for reducing the Fehling solution.

For conducting the present invention, the starting material pentoses are required to be those in which the first position readily suffering an attack by microorganisms is always protected by an alkyl group. Such protection is usually made by methylation but other alkylation such as ethylation may also be used. Such a protection method may be based on the method of methylation of glucose which is a hexose (Experimental Text of Agricultural Chemistry, Vol. 2, pp 704-707, published on 1957 by Sangyo Tosho K.K. Japan). As methylpentoside, two kinds, α- and β-types exist. As mentioned above, since the methyl group is left off by means of the post-treatment after the fermentation, either of α- or β-type may be used.

With respect to D- and L-types of pentose, there is no particular limitation but generally speaking, D-type is better for the multiplication of microorganisms.

As microorganisms suitable for use, there are enumerated, those for producing keto acids from glucose such as oxidizing microorganism including genera of Gluconobacter, Pseudomonas, Erwinia, Seraccia, etc.

As nitrogen source to be used in the culture medium, organic nitrogen source such as meat extract, polypeptone, yeast extract, malt extract, soy bean cake extract, cornsteep liquor, cotton seed cake and the like, and inorganic nitrogen source such as ammonium salts, nitrate, etc. may be used alone or in admixture.

As auxiliary factors for multiplication of microorganisms, a lower concentration, each of glucose, glycerine, acetate, etc. may be added.

The fermentation is carried out at a temperature of 25°-37° C., and generally preferable at around 30° C., and usually the culture is completed within 2-7 days.

The fermentation-completed solution is heated under an acidic condition to form γ-pyrones. For acidification of the solution, mineral acids such as sulfuric acid, nitric acid, hydrohalogenic acid, etc., or organic acids such as acetic acid or the like are used. In this case, pH 0.5-5.0 especially 0.5-4.0 is preferred. Heating is carried out for 80°-120° C.; frequently 5°-120° C.

As recovery of γ-pyrones from the fermentation solution, the solution is once concentrated and dried up, and then the resultant is extracted under warm or heating condition by using γ-pyrone-soluble organic solvents such as chloroform, benzene, toluene, xylene, alcohols (methanol, ethanol, etc.) or the like, and thereafter, the resultant is again concentrated and dried out, and finally a fractionation-recrystallization is carried out.

PREFERRED MODES OF THE INVENTION

The present invention is further explained by describing the following working examples. However, in view of numerous combinations of kinds of microorganisms and pentoses, it is impossible to disclose such numerous number of the working examples. Accordingly, the followings are only a small number of the working examples, but these should not limit the present invention.

EXAMPLE 1

100 ml of culture medium composed of 3.64 g of α-methylxyloside (prepared according to the method described in "Experimental Text of Agricultural Chemistry" Vol. 2, page 704, published by Sangyo Tosho K.K.), 1.5 g of glycerine, 1.5 g of yeast extract (manf. by Oriental Yeast K.K.), 1.5 g of polypeptone (manf. by Nippon Seiyaku K.K.) 0.75 g of $CaCO_3$, which were sterilized at 160° C. for 3 hrs. beforehand) was charged into 500 ml Sakaguchi flask and sterilized at 120° C. for 15 minutes. Then, strain of Gluconobacter rubiginosus IFO 3244 was incubated therein, and shake-cultured at 30° C. for 6 days. The cultured solution was sterilized, and then the resulting culture solution filtrate was adjusted to pH 1.0 with sulfuric acid, followed by heating at 120° C. for 30 minutes, and then filtered again at 90°–96° C. The resulting filtrate was concentrated in vacuo to be dried out. After that, the resultant was extracted into two lines with 100 ml of chloroform under warm condition and then the resulting extract solution was concentrated to obtain crude crystals. The crystals were further recrystallized with 50% methanol to obtain 0.1 g of white needle-like crystals. This product was identified to be pyrocomenic acid by means of IR spectrum analysis.

After the mother liquor from which the above crude crystal was recovered, was concentrated, the resulting concentrate was subjected to a fractionation thin layer chromatography (available from Merck Co., Ltd., silica gel 60, eluent solvent system chloroform: ethanol=10:1), and a fraction in Rf lower than pyrocomenic acid was collected while checking it by aid of $Fe^{3+}$ coloring. The collected fraction was extracted with chloroform, and then concentrated in vacuo to be dried up. The resultant was recrystallized with 50% methanol to obtain 0.03 g of white crystal. This product is found to be rubiginol by means of IR spectrum analysis.

The above results are shown in Table 2.

TABLE 2

| Fermentation progress and amounts of pyrocomenic acid production | | | | |
|---|---|---|---|---|
| Permentation period | 0 | 2 | 4 | 6 |
| pH of fermentation solution | | 5.0 | 4.9 | 4.9 |
| Fehlings solution reductivity*[1] | 0 | 788 | 863 | 900 |
| Amounts of pyrocomenic acid production*[2] | 0 | 250 | 550 | 670 |

*[1] asked as glucose-corresponding amount according to the Bertrand method.
*[2] asked according to the method described downward in Table 1.

EXAMPLE 2

A culture medium containing 3.64 g of α-methylxyloside was prepared likewise in Example 1. 100 ml thereof was charged into a 500 ml Sakaguchi's flask, then sterilized, and Gluconobacter melanogenus IFO 3293 was incubated therein to carry out the vibration culture at 30° C. for 5 days, which was followed by the treatment according to that of Example 1 to obtain 0.1 g of pyrocomenic acid and 0.05 g of rubiginol.

EXAMPLE 3

A culture medium containing 2 73 g of α-methyl-D-lyxoside was prepared likewise in Example 1, and 100 ml thereof was charged into a 500 ml Sakaguchi's flask, then sterilized and Gluconobacter rubiginosus IFO 3244 was incubated therein, which was followed by the vibration culture at 30° C. for 6 days. The resulting culture solution was sterilized and then the resulting culture solution filtrate was adjusted to pH 4.0 with sulfuric acid and thereafter heated at 100° C. for 60 minutes. The post-treatment was carried out according to Example 1 to obtain 0.2 g of pyrocomenic acid and 0.02 g of rubiginol.

EXAMPLE 4

A culture medium containing 2.73 g of α-methyl-D-riboside was prepared likewise is Example 1, and 100 ml thereof was charged into a Sakaguchi's flask and sterilized. Gluconobacter rubiginosus IFO 3244 was incubated therein, which was followed by a vibration culture at 30° C. for 10 days. The post-treatment was carried out according to Example 3 to obtain 0.01 g of pyrocomenic acid and a trace of rubiginol.

EXAMPLE 5

A culture medium containing 3.28 g of α-methyl-D-arabinoside was prepared in the same manner as in Example 1, and 100 ml thereof was charged into a Sakaguchi's flask and then sterilized. Gluconobacter rubiginosus IFO 3244 was incubated therein, which was followed by a vibration culture at 30° C. for 6 days. The post-treatment was carried out according to Example 3 to obtain 0.2 g of pyrocomenic acid and 0.05 g of rubiginol.

EXAMPLE 6

100 ml of culture medium having pH 6.7–7.0, which was composed of 0.5 g of glucose, 0.5 g of lycerol, 0.5 g of yeast extract, 0.1 g of magnesium sulfate was dividedly poured into 20 test tubes, respectively. After they were sterilized at 120° C. for 15 minutes, one Pt-wire loop of Gluconobacter suboxydans was incubated therein and then subjected to a vibration culture at 30° C. for 20 hrs. (pre-culture solution). 900 ml of a culture medium composed of 72.8 g of α-methyl-D-xyloside, 30 g of glycerine, 30 g of yeast extract, 30 g of polypeptone and 15 g of $CaCO_3$ (added after separately sterilizing at 160° C. for 3 hrs) was dividedly poured into ten Sakaguchi's flasks (500 ml volume), i.e. an aliquot quantity of 90 ml, and they were sterilized at 120° C. for 15 minutes. After that, said pre-culture solution was dividedly added to the 10 flasks in an amount of each 10 ml per a flask, which were followed by a vibration culture at 30° C. for 2 days. The resulting culture-completed solution was added with 1 g of an active charcoal, and then subjected to a suction-filtration on a sellire, the resulting culture solution filtrate was added with 20 ml of hydriodic acid, further adjusted to pH 1.0 with sulfuric acid and then heated at 96° C. for 60 minutes. Heating was further continued at 120° C. for 30 minutes and then the resultant was filtered at 90°–96° C. The filtrate was concentrated in vacuo up to a silap-like state, which was added with 100 ml of methanol and left as it was, to obtain 30 g of crude pyrocomenic acid. This was recrystallized with 50% methanol to obtain 20 g of pure pyrocomenic acid. On the other hand, the mother liquor remaining after the recovery of pyrocomenic acid was gathered and concentrated in vacuo. To the concentrate 100 ml of methanol was added and then left as it was in a refrigerator to obtain 3 g of crude rubiginol, which was further recrystallized with 50% methanol to obtain 2 g of pure rubiginol.

We claim:

1. A process for the preparation of 3-hydroxy-4(1H)-pyran-4-one and 3,5-dihydroxy-4(1H)-pyran-4-one, which comprises fermenting a 1-alkyl-substituted-aldopentose with a microorganism selected from the group consisting of *Gluconobacter rubiginosus, Gluconobacter melanogenus, Gluconobacter suboxydans, Erwinia carotovora,* and *Pseudomonas fluorescens;* heating the resultant ferment under acid conditions; and recovering 3-hydroxy-4(1H)-pyran-4-one and 3,5-dihydroxy-4-(1H)-pyran-4-one from the heated and acidified ferment.

2. The process according to claim 1, wherein the 1-alkyl-substituted-aldopentose is xylose, arabinose, lyxose or ribose.

3. The process according to claim 1, wherein the 1-alkyl-substituted-aldopentose is a methyl- or ethyl-substituted-aldopentose.

4. The process according to claim 1, wherein the 1-methyl-substituted-aldopentose is α-methylxyloside, α-methyl-D-lyxoside or α-methyl-D-riboside.

* * * * *